United States Patent
Tam et al.

Patent Number: 6,084,937
Date of Patent: Jul. 4, 2000

[54] ADAPTIVE MASK BOUNDARY CORRECTION IN A CONE BEAM IMAGING SYSTEM

[75] Inventors: Kwok C. Tam, Edison; Ali Bani-Hashemi, Belle Mead, both of N.J.

[73] Assignee: Siemens Corporate Research, Inc., Princeton, N.J.

[21] Appl. No.: 09/162,303

[22] Filed: Sep. 28, 1998

Related U.S. Application Data

[63] Continuation-in-part of application No. 09/123,574, Jul. 27, 1998.

[51] Int. Cl.⁷ .................................................. A61B 6/03
[52] U.S. Cl. ........................... 378/4; 378/8; 378/901
[58] Field of Search .......................... 378/4, 8, 15, 94

[56] References Cited

U.S. PATENT DOCUMENTS

| | | | |
|---|---|---|---|
| 5,390,111 | 2/1995 | Tam | 378/16 |
| 5,390,226 | 2/1995 | Tam | 378/19 |
| 5,504,792 | 4/1996 | Tam | 378/15 |
| 5,878,103 | 3/1999 | Sauer et al. | 378/15 |
| 6,018,561 | 1/2000 | Tam | 378/4 |

*Primary Examiner*—David V. Bruce
*Attorney, Agent, or Firm*—Lawrence C. Edelman

[57] ABSTRACT

A method and apparatus for three dimensional (3D) computerized tomographic (CT) imaging of a region-of-interest (ROI) in an object, wherein image reconstruction processing is applied to a plurality of sets of 2D cone beam projection data, each set being acquired on a 2D detector at a corresponding plurality of scan path source positions. A first image reconstruction processing step comprises applying a mask to each set of the projection data so that data inside the boundaries of each mask form a corresponding plurality of masked 2D data sets. Next, the data inside each masked 2D data set is filtered along a plurality of parallel lines formed therein, to generate a corresponding plurality of filtered 2D data sets. Each filtered 2D data set corresponds to a calculation of a first estimate of Radon derivative data determined from a given set of the 2D cone beam projection data. The next step comprises adaptively developing 2D correction data for each of the first estimates of Radon derivative data. The final step comprises combining each filtered 2D data set and the adaptively determined 2D correction data calculated therefore, in a weighted 3D backprojection manner into a 3D space, thereby reconstructing a 3D image of the ROI in the object.

34 Claims, 8 Drawing Sheets

ADAPTIVE MASK BOUNDARY CORRECTION IN A CONE BEAM IMAGING SYSTEM

CROSS-REFERENCE TO RELATED APPLICATIONS

This is a continuation-in-part of application Ser. No. 09/123,574, filed Jul. 27, 1998.

BACKGROUND OF THE INVENTION

1. Field of the Invention

The invention relates generally to 3D image reconstruction in a cone beam x-ray imaging system, and more specifically to an adaptive simplification for the correction of image inaccuracies caused by mask boundaries when using a simplified 3D backprojection image reconstruction technique.

2. Description of the Prior Art

A filtered backprojection (FBP) cone beam image reconstruction technique is described by Kudo, H. and Saito, T., in their article entitled "Derivation and Implementation of a Cone-Beam Reconstruction Algorithm for Nonplanar Orbits", IEEE Trans.Med. Imag., MI-13 (1994) 196–211, incorporated herein by reference.

Briefly, the FBP technique consists of the following steps at each cone beam view (i.e., at each position of the radiation source as it scans about the object, and at which an imaging detector acquires a corresponding set of projection data):

1. Compute a 1D projection (i.e., line integral) of the measured cone beam image acquired on a detector plane 1 at each of a plurality of angles θ. This step is illustrated by FIG. 1A for a given angle $\theta_1$ of a plurality of angles θ, where the projection 2 at coordinates (r,θ) comprises the integrated values of the cone beam image 4 on detector plane 1 along a plurality of parallel lines L(r, θ) that are normal to angle θ, each line L being at an incremental distance r from an origin O. Generally, if the detector plane 1 comprises an N by N array of pixels, then the number of angles θ is typically given by πN/2.

2. Filter each 1D projection in accordance with a d/dr filter, resulting in a new set of values at each of the r,θ coordinates, such as shown by filtered projection 6 for the angle $\theta_1$ in FIG. 1A.

3. Normalize the filtered projections with a normalization function M(r,θ). Normalization is needed to take into account the number of times the plane of integration Q(r,θ) which intersects the source position and the line L(r,θ), intersects the scan path, since the data developed at each scan path intersection creates a contribution to the image reconstruction on the plane Q(r,θ).

4. Backproject the filtered projection 6 from each angle θ into a 2D object space 7 which coincides with the detector plane 1. This step is illustrated by FIG. 1B, wherein lines 8 spread the value from each r,θ coordinate into 2D space 7 in a direction normal to each θ.

5. Perform a 1D d/dt filtering of the backprojection image formed in 2D space 7 by step 4. The ID filtering is performed in the direction of the scan path, i.e., along lines 10, where t points in the direction of the scan path.

6. Perform a weighted 3D backprojection of the resulting data in 2D space 7 (i.e., from each pixel in the detector) onto a plurality of sample points P in a 3D object volume 12. The density assigned to each point P is weighted by the inverse of the square of the distance between the point and the spatial coordinates of the x-ray source (see Equation (59) of the forenoted Kudo et al article).

The above prior art procedure will be referred to hereinafter as the 6-step process. It is assumed in this process that the entire cone beam image of the object is captured on the detector of the imaging system. Consider a plane Q(r,θ), which intersects the object, formed by the source and the line L(r,θ) on the detector at angle θ and at a distance r from the origin. Ignoring the function M(r,θ), the operations 1 through 6 compute the contribution to the reconstructed object density on the plane Q(r,θ) from the x-ray data illuminating the plane and its immediate vicinity. Since the 6-step process is detector driven, a contribution from the data illuminating the plane is computed every time the plane intersects the scan path and thus is illuminated by the x-ray beam. Consequently, the function M(r, θ) is used after the filter function in step 2 to normalize the results. Normalization is particularly undesirable since it requires pre-computing and storing a 2D array M(r, θ) for each source position along an imaging scan path. Since there are usually hundreds, if not thousands of source positions, this type of normalization is both computationally intensive and resource (computer memory) expensive. In the Kudo et al article, however, at page 203 it is noted that in the special case where the scan path is a circle, steps 1–5 can be simplified into a single convolution step, which essentially comprises ramp filtering the cone beam image in the direction of the scan path. This ramp filtering is equivalent to the well-known Feldkamp algorithm for a single circular orbit, such algorithm being described in particular detail in the article by L. A. Feldkamp, L.C. Davis, and J. W. Kress, entitled "Practical cone-beam algorithm" published in the J. Opt. Soc. Am. A. Vol. 1, 1984, pages 612–619, incorporated by reference herein (see in particular the convolution function equations 15 and 16 at page 614, which describe the convolution function as:

$$g(Y) = \text{Re} \int_0^{\omega_y 0} \exp(i\omega Y)\omega d\omega).$$

The key to this simplification is that in the special case of a circular scan path, the normalization function M(r, θ) is a constant, equal to 2. Consequently, the filtered projection at each r, θ that results after step 2, can merely be divided by 2 to compensate for the data redundancy.

K. Tam's prior U.S. patent application Ser. No. 09/106,537 entitled SIMPLIFIED CONE BEAM IMAGE RECONSTRUCTION USING 3D BACKPROJECTION, filed Jun. 29, 1998 and incorporated herein by reference, describes how to use this ramp filter simplification for image reconstruction in a cone beam imaging system having source scan paths other than a single circle, such as a spiral scan path, and furthermore, in a cone beam imaging system having a short detector, i.e., a detector that captures only a portion of the 2D cone beam image at each cone beam view (i.e., at each source position). As described in greater detail in this forenoted prior U.S. Patent Application, a simplified "3-step" technique comprises:

1) applying a mask to each set of 2D cone beam projection data acquired at each source position, thereby forming a masked 2D data set for each source position,
2) ramp filtering the 2D cone beam projection data inside each masked 2D data set, forming ramp filtered 2D data sets, and
3) subjecting the ramp filtered 2D data sets to a weighted 3D backprojection into a 3D space corresponding to a complete field of view of a region of interest (ROI) of the object, thereby reconstructing in the 3D space a 3D image of the ROI in the object.

A key part of this prior invention is the masking process. The masking allows the image reconstruction processing to be greatly speeded-up due to a reduced need for extensive computations, elimination of the requirement for normalization step 3 of the 6-step process (thereby obviating the need for significant memory allocation for normalization factors), and furthermore, the imaging system can use a short detector, i.e., one that does not acquire at each source position a complete view of the ROI of the object.

K. Tam's prior invention can be considered as applying masking to steps 1 through 5 of the Kudo et al 6-step process, followed by step 6. The application of masking to Kudo et al's steps 1 and 2 is conceptually equivalent to the following operations:

m1) compute the integrals on line segments bounded by the mask, and m2) compute the difference between the line integrals so computed on adjacent parallel line segments.

It is intended that steps m1 and m2 yield a quantity proportional to the Radon derivative for the portion of plane $Q(r,\theta)$ defined by the current source position and the prior and the subsequent source positions. The angular ranges for various portions of plane $Q(r,\theta)$ are illustrated in FIG. 3, and will be described in greater detail later herein.

The operations in steps m1 and m2 are illustrated in FIG. 4. As shown therein, L, $L_1'$ and $L_2'$ are three closely spaced parallel line segments that are bound by a mask 400, where L is midway between $L_1'$ and $L_2'$. Line segment L is representative of many such line segments formed at various angles in mask 400, and corresponds to the previously described lines $L(r,\theta)$ of FIG. 1A and lines 8 of FIG. 1B, as well known to those skilled in this technology, which are used for computing Radon derivative data from the cone beam projection data. In the present technique, the arithmetic difference between the integrals computed for a given pair of line segments $L_1'$ and $L_2'$ in mask 400 is determined, and corresponds to the Radon derivative of the partial plane defined by the line segment L and the current source position, up to a multiplicative constant. In reality, however, this masking method yields only an approximation of the Radon derivative of the partial plane. This is because, as described in K. Tam's recently issued U.S. Pat. No. 5,748,697, the Radon derivative for the relevant portion of plane $Q(r, \theta)$ should be computed as shown in FIG. 5 herein. As evident from FIG. 5, line segment L is the same as that shown in FIG. 4, however line segments $L_1$ and $L_2$ are obtained by orthogonal translation of L, as they should be. Accordingly, contrary to what is shown in FIG. 4, the ends of line segments $L_1$ and $L_2$ shown in FIG. 5 are not bound by mask 500. The ending of the line segments at the boundaries of the mask is referred to herein as "hard masking". As a consequence of the hard masking, the arithmetic difference between the integrals computed on line segments $L'_1$ and $L'_2$ does not yield an exact Radon derivative, i.e., one only differing only by a multiplicative constant.

K. Tam's U.S. patent application Ser. No. 09/123,574 filed Jul. 27, 1998 describes a technique for computing 2D correction data which, when combined with the ramp filtered 2D approximation data sets, yields an exact image reconstruction. However, the 2D correction data requires 3D backprojection from a virtual detector which covers the entire object, instead of from the actual detector. The virtual detector is usually much larger than the actual detector and therefor the signal processing for accomplishing the 3D backprojection of the 2D correction data is significantly greater than it is for the approximation data.

It would be desirable to reduce the amount of correction data related signal processing needed to develop an exact image reconstruction, without significantly affecting the exactness of the image reconstruction.

SUMMARY OF THE INVENTION

A method and apparatus for three dimensional (3D) computerized tomographic (CT) imaging of a region-of-interest (ROI) in an object, wherein image reconstruction processing is applied to a plurality of sets of 2D cone beam projection data, each set being acquired on a 2D detector at a corresponding plurality of scan path source positions. A first image reconstruction processing step comprises applying a mask to each set of the projection data so that data inside the boundaries of each mask form a corresponding plurality of masked 2D data sets. The next step comprises ramp filtering of the data inside each masked 2D data set along a plurality of parallel lines formed therein, to generate a corresponding plurality of filtered 2D data sets. Each filtered 2D data set corresponds to a calculation of a first estimate of Radon derivative data determined from a given set of the 2D cone beam projection data. The next step comprises adaptively developing 2D correction data for each of the first estimates of Radon derivative data. The final step comprises combining each filtered 2D data set and the adaptively determined 2D correction data calculated therefore, in a weighted 3D backprojection manner into a 3D space, thereby reconstructing a 3D image of the ROI in the object.

DETAILED DESCRIPTION OF THE INVENTION

Figure 2:
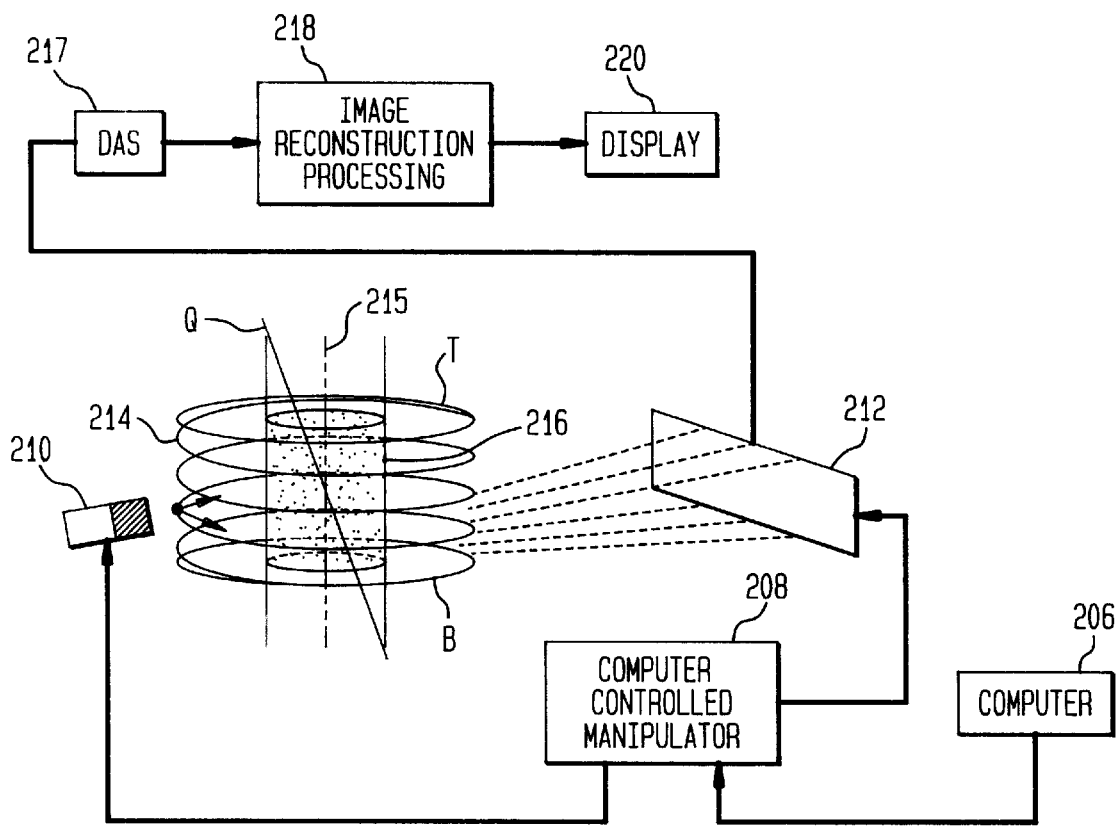
FIG. 2 illustrates a cone beam imaging apparatus useful for performing image reconstruction in accordance with the principles of the invention.

FIG. 2 illustrates a cone beam 3D CT imaging apparatus useful for acquiring and processing acquired projection data in accordance with the principles of the present invention. The illustrated imaging apparatus is constructed and operates substantially in accordance with the same principles described in U.S. Pat. No. 5,257,183 entitled METHOD AND APPARATUS FOR CONVERTING CONE BEAM X-RAY PROJECTION DATA TO PLANAR INTEGRAL AND RECONSTRUCTING A THREE-DIMENSIONAL COMPUTERIZED TOMOGRAPHY (CT) IMAGE OF AN OBJECT issued Oct. 26, 1993, and U.S. Pat. No. 5,453,666 entitled HELICAL AND CIRCLE SCAN REGION OF INTEREST COMPUTERIZED TOMOGRAPHY issued Oct. 31, 1995, both incorporated herein by reference, except as to be specifically described later with respect to implementation of image reconstruction processing in accordance with the present invention.

As shown in FIG. 2, in response to control signals from an appropriately programmed computer 206, a computer controlled manipulator 208 causes a source 210 of a cone or pyramid shaped beam of energy (such as x-rays) and a two-dimensional pixelated detector array 212 to cooperate (scan) at a plurality of discreet, sequentially occurring, adjacent source positions along a pre-defined source scanning path. In the illustrated embodiment the scanning path is shown as a spiral scan path 214 centered on a predetermined axis 215 of an object 216. Other types of scan paths that encircle and traverse object 216 can also be used, however, as will become apparent later, a scan path 214 exhibiting a high degree of symmetry in its parallel projection is preferred.

The only height requirement on the detector is that it should be more than the distance between adjacent turns of a projection of the spiral scan path on the detector. If only a region of interest (ROI) in object 216 is to be imaged, in a preferred embodiment, the known technique of providing a top circle scan T at the top level of the ROI and a bottom circle scan B at the bottom level of the ROI, are added.

As a result of the source/detector cooperation under control of computer 206 and manipulator 208, at each of the source positions along path 214, x-ray energy passes through the field of view of the imaging apparatus, is attenuated by object 216, and a set of projection data corresponding to the sensed x-ray energy falling on the elements (pixels) within detector 212 is developed. Each set of projection data is supplied to a data acquisition system (DAS) 217 which, like the previously described portions of FIG. 2, may operate in a fashion well known to those of ordinary skill in this technology for digitizing and storing of the acquired projection data.

In the above-noted U.S. Pat. Nos. 5,257,183 and 5,453,666, image reconstruction processing 218 is provided by Radon space driven conversions, thereby developing an image reconstruction of object 216 on a display 220. The present inventor has devised a way to incorporate the technique of data combination for ROI reconstruction, with the Kudo et al. image reconstruction processing simplification for a single circle scan imager, thereby providing a cone beam imaging system that can not only have a spiral scan path, but can also use a short detector. Instead of division by the function $M(r, \theta)$ as done by Kudo et al., in the present invention normalization of the reconstructed object densities is achieved by dividing the x-ray beam coverage of plane $Q(r, \theta)$ between the various source positions that illuminate the plane without any overlap. Consequently, the image reconstruction processing in accordance with the invention is greatly speeded-up due to a reduced need for extensive computations, the requirement of significant memory allocation for normalization step 3 is obviated, and furthermore, the imaging system can use a shorter detector, i.e., one that does not acquire at each source position a complete view of the ROI of the object.

Figure 3:
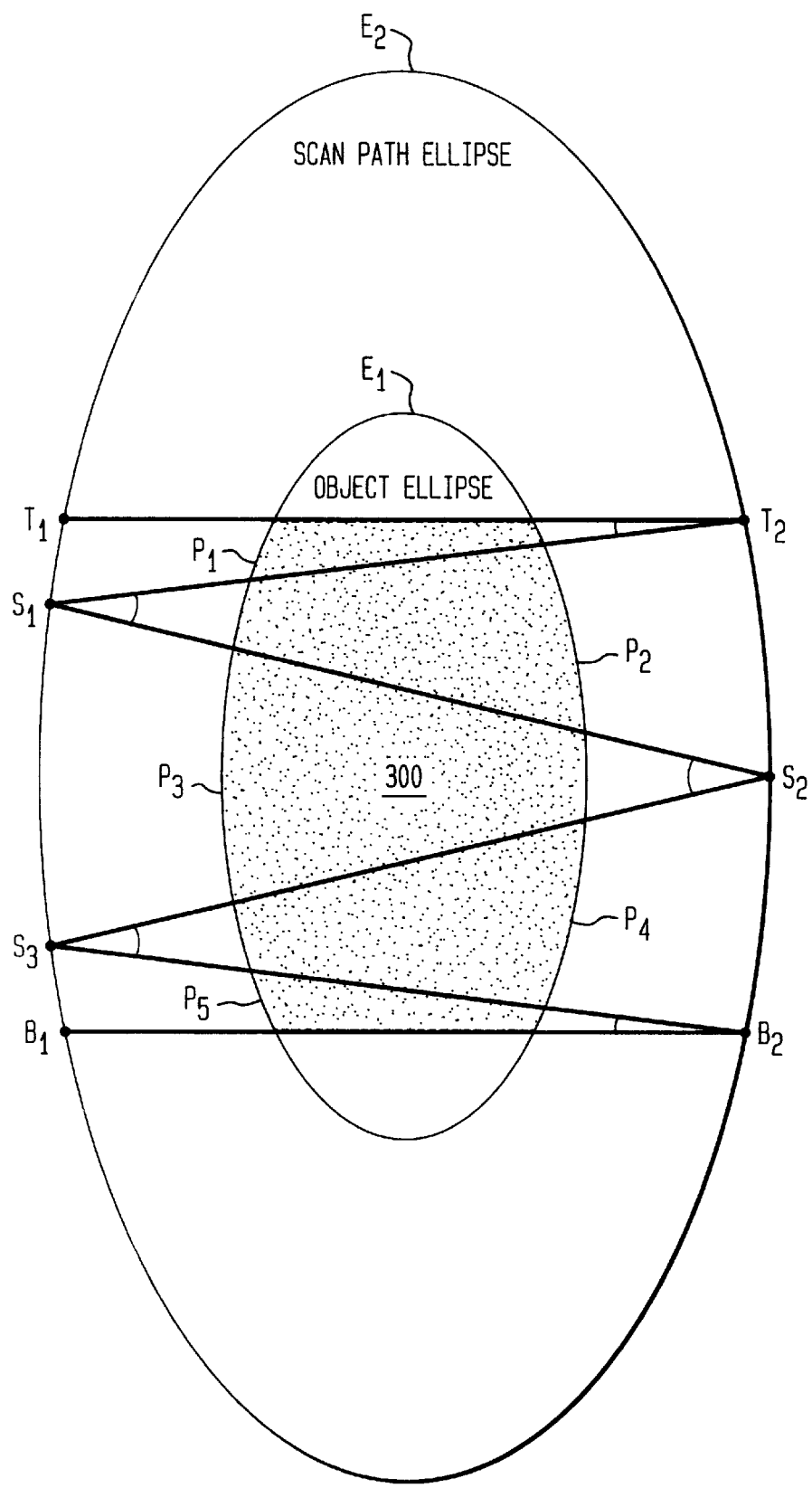
FIG. 3 illustrates a procedure for data combination when performing image reconstruction in accordance with the present invention.

More specifically, this concept of the division of x-ray beam coverage is illustrated in FIG. 3, which represents a typical integration plane $Q(r, \theta)$ intersecting cylindrical object 216 and the spiral scan path 214, which is assumed to wrap around an ROI in object 216 on an imaginary cylinder. An edge view of plane Q is illustrated in FIG. 3. Since a non-vertical plane will intersect a cylinder in an ellipse, the plane $Q(r, \theta)$ intersects object 216 and the cylindrical spiral scan path 214 in two ellipses, one inside the other.

The intersection of the integration plane Q with the object cylinder is indicated by the smaller ellipse E1, and its intersection with the scan path cylinder is indicated by the larger ellipse E2. Since spiral path 214 lies on the scan path cylinder, it intersects the plane Q in points that lie on the ellipse E2. These source positions are shown as S1, S2, and S3 in the FIG. 3. Similarly, it is easy to see that the top scan path circle intersects the plane in two points T1 and T2 which lie at the intersection between E2 and the top edge of the object's region-of-interest (shaded portion of object 216), and that the bottom circle intersects the plane in the two points B1 and B2 which lie at the intersection between E2 and the bottom edge of the object's region-of-interest. Other integration planes may have more or less spiral scan path intersections, depending upon their orientation, and may not intersect either of the top or the bottom circle scan paths.

As is apparent from FIG. 3, the source positions which illuminate that portion of integration plane Q that lies within the ROI (shaded area 300), are $T_2$, $S_1$, $S_2$, $S_3$, and $B_2$. Complete X-ray coverage of region-of-interest 300 of this portion of the integration plane can be achieved by suitably combining the data acquired at these 5 source positions, as indicated in FIG. 3. For example, at $T_2$ we only use the cone beam data within the angle bound by $T_1T_2$ and $S_1T_2$, and at $S_1$ we only use the cone beam data within the angle bound by $T_2S_1$ and $S_2S_1$. And so on. Five partial planes P1 through P5 are therefore defined by the source positions $T_2$, $S_1$, $S_2$, $S_3$, and $B_2$, which do not overlap and together completely cover the portion of plane Q that lies within ROI 300. In this way the totality of the cone beam data from each of the contributing source positions illuminates the entire plane $Q(r,\theta)$ only once without any overlap. Further details of this data combination technique can be found in K. Tam's earlier cone beam patents, such as U.S. Pat. No. 5,463,666.

Because only specific non-overlapping contributions to the Radon data are developed from the projection data, the function $M(r,\theta)$ can be set to unity for all cone beam views. Thus, as the cone beam projection data acquired by the detector at each of the source positions is processed, as next described, contributions to each plane intersecting the ROI are developed only once.

Figure 4:
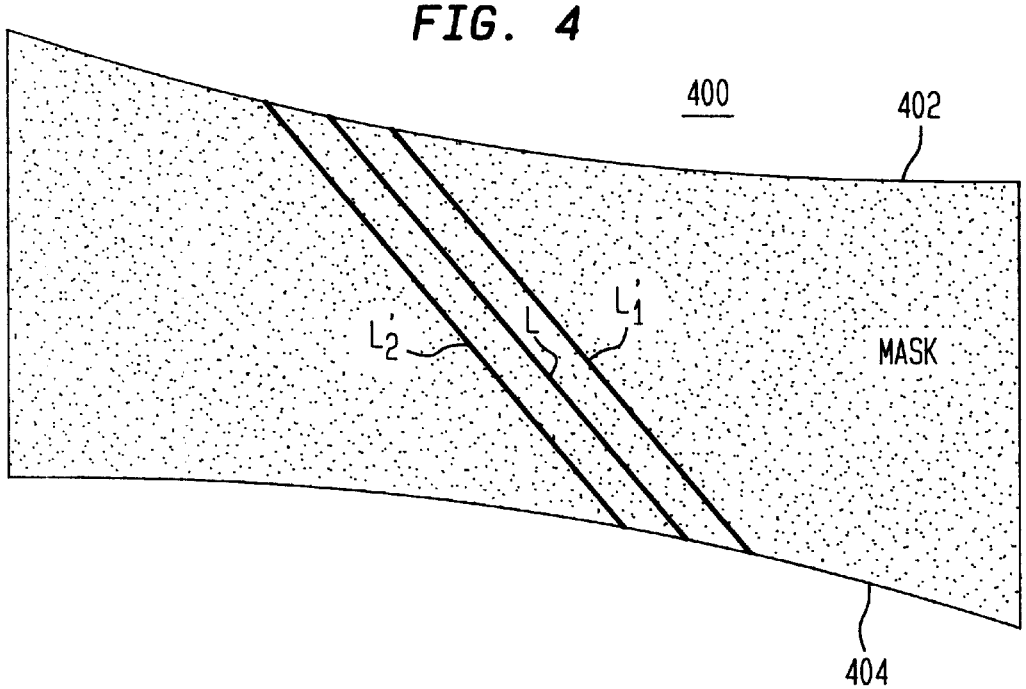
FIGS. 4 and 5 illustrate hard and soft masking, respectively, each technique useful for developing Radon derivative data from the acquired cone beam projection.

As described above in conjunction with FIG. 3, the acquired cone beam projection data should be restricted to the appropriate angular range to avoid data redundancy, and thereby avoid the need for Kudo et al's normalization function $M(r,\theta)$. For image reconstruction in accordance with the present invention, this is accomplished using a masking process. In general, the masking of acquired cone beam projection data is well known, for example see K. Tam's earlier U.S. Pat. No. 5,504,792 issued Apr. 2, 1996. FIG. 4 illustrates one such mask 400. Mask 400 consists of a top curve 402 and a bottom curve 404, each curve being formed by cone beam projections of the spiral scan path turn above and the spiral scan path turn below the current source position, onto the detector (212 of FIG. 2). For a flat detector located at the rotation axis such that a line connecting the source to the detector origin is normal to the detector plane, the equation for top curve 402 for the spiral scan path projection is given by:

$$y = \frac{h}{2\pi}\tan^{-1}\left(\frac{a}{x}\right)\left(1 + \frac{x^2}{a^2}\right) \quad \text{for } x \geq 0 \quad (1)$$

$$y = \frac{h}{2\pi}\left[\pi + \tan^{-1}\left(\frac{a}{x}\right)\right]\left(1 + \frac{x^2}{a^2}\right) \quad \text{for } x < 0$$

where x and y are the Cartesian coordinate axes of the detector, with the y axis coinciding with the rotation axis, a is the radius of the spiral, and h is the distance between adjacent spiral turns (the pitch). Bottom curve 404 is a reflection of top curve 402 about the origin, i.e., $$(x, y) \Rightarrow (-x, -y).$$

Figure 6:
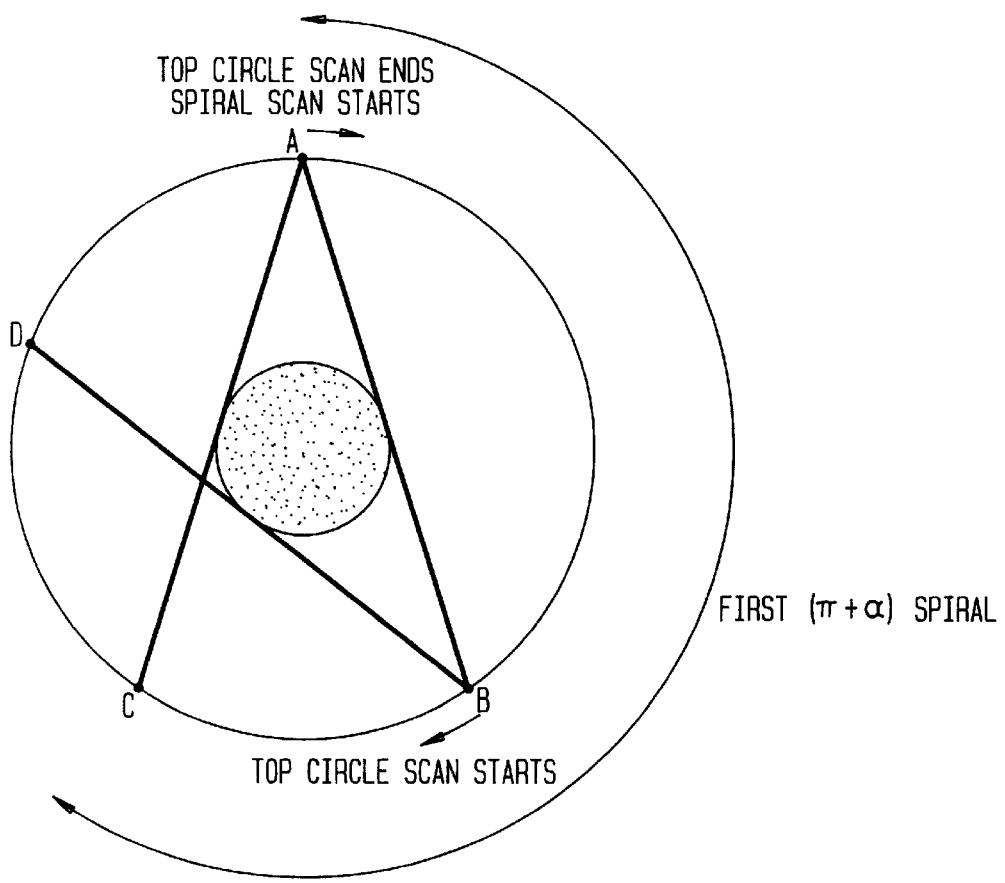
FIG. 6 is useful for understanding the generation of the masks shown in FIGS. 4,5 and 7–10.
Figure 7:
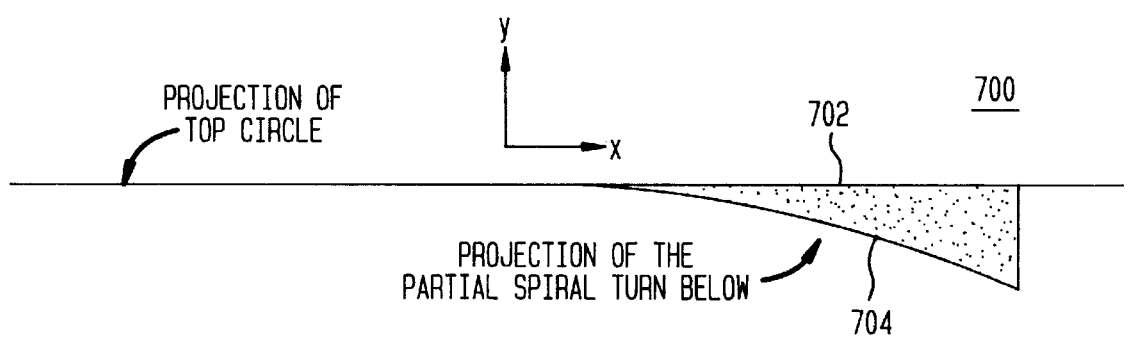
FIGS. 7 and 8 illustrate the shape of the masks that are used at source positions near the top and bottom of the spiral scan path shown in FIG. 2.
Figure 8:
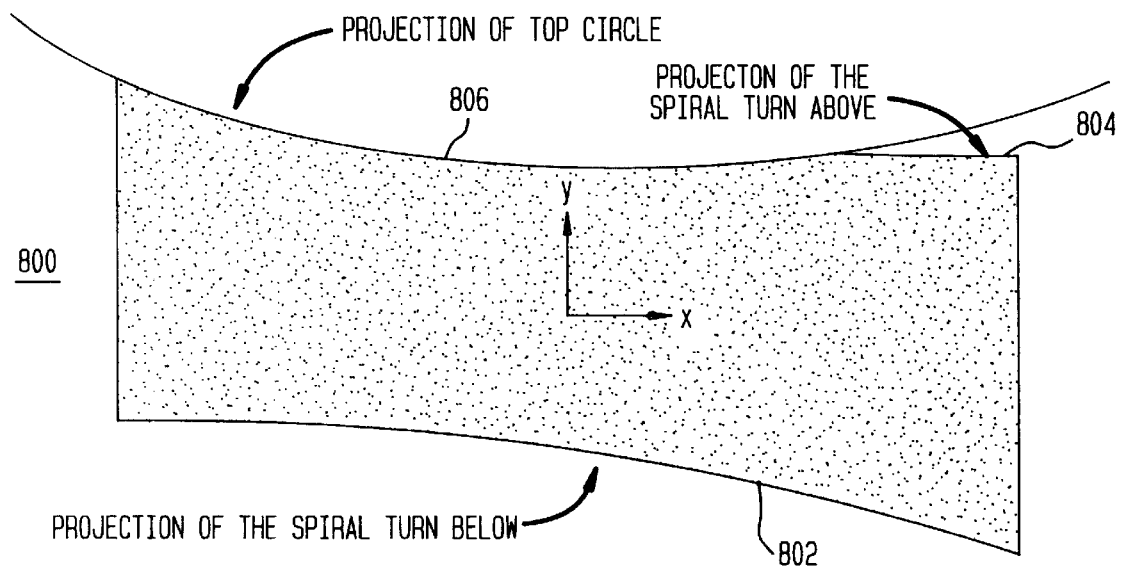

As described in conjunction with FIG. 2, for ROI imaging, circular arc scans are needed at the top and bottom levels. The top circle scan T starts at the angle $(\pi+\alpha)$ before the start of the spiral scan, and the bottom circle scan B ends at the angle $(\pi+\alpha)$ after the end of the spiral scan, where a is the fan angle of the x-ray beam. The detailed geometry of the mask used at each source position depends on the location of the source in the scan path. Accordingly, one can divide the spiral scan path into 5 distinct regions, as illustrated in FIG. 6. The first region comprises the last $(\pi+\alpha)$ turn of the top circle (clockwise from B to A). The second region comprises the first $(\pi+\alpha)$ turn of the spiral (clockwise from A to C). The third region comprises the interior portion of the spiral, i.e. after the first $(\pi+\alpha)$ turn and before the last $(\pi+\alpha)$ turn. The fourth region comprises the last $(\pi+\alpha)$ turn of the spiral (similar to the second region). The fifth region comprises the first $(\pi+\alpha)$ turn of the bottom circle (similar to the first region, but at the bottom). The masks for these 5 regions are described in greater detailed below, and are illustrated in FIGS. 7–8. These Figures assume the radiation source rotates in a spiral path from top to bottom in a clockwise direction.

(1) For the last $(\pi+\alpha)$ turn of the top circle, see mask 700 of FIG. 7, wherein:

The top curve is a horizontal line at the level of the top circular arc; and

The bottom curve is a reflection of Equation (1) about the origin.

(2) For the first $(\pi+\alpha)$ turn of the spiral, see mask 800 of FIG. 8, wherein:

The top curve is the intersection of two curves: the standard top spiral mask, Equation (1), and the cone beam projection of the top circle projected from the source given by the equation:

$$y = b\left(1 + \frac{x^2}{a^2}\right),$$

where 2b is the distance between the top and bottom circles; and

The bottom curve is a reflection of Equation (1) about the origin.

(3) For the interior portion of the spiral, see mask 400 of FIG. 4, wherein:

The top curve described by Equation (1); and

The bottom curve is a reflection of Equation (1) about the origin.

(4) For the last $(\pi+\alpha)$ turn of the spiral, see mask 800 of FIG. 8, but rotated by 180°.

(5) For the first $(\pi+\alpha)$ turn of the bottom circle, see mask 700 of FIG. 7, but rotated by 180°.

A first step of image reconstruction comprises bounding the set of projection data acquired by the detector at each source position with an appropriate mask, such as one of the masks of FIGS. 4 and 7–8. In accordance with the general principles of masking, data in the set that is outside the mask is assumed to have a zero value, while the value of the data that is inside the mask is left unchanged. After a set of projection data is appropriately masked, it is referred to as a masked set of projection data, or more simply as a masked data set. Since the masks are formed by cone beam projection of the spiral turn above and the turn below the current source position, the masked data set corresponds exactly to the angular range bound by the prior and the subsequent source positions, as required by the data combination principles illustrated in FIG. 3. Computer 206 of FIG. 2 can compute the masks "on-the-fly" during image reconstruction, or they could be pre-calculated and stored in system memory.

Figure 9:
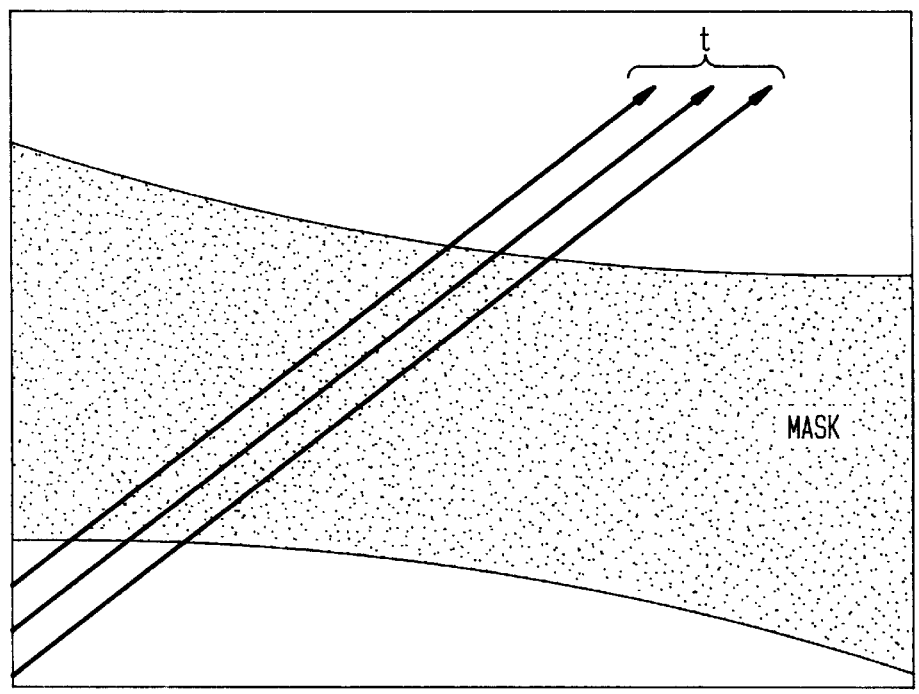
FIG. 9 illustrates ramp filtering of a masked data set.

Next, the Feldkamp ramp filtering technique is applied to the masked sets of projection data, thereby simplifying steps 1 through 5 of the prior art 6-step process into a single ramp filtering step, as illustrated in FIG. 9. More specifically, each set of masked data is ramp filtered along a plurality of parallel lines (t) formed therein, which lines are parallel with and in the direction of a parallel projection into the data set of a line that is tangent to the scan path at the source position that acquired that data set and in the direction of the next source position. Ramp filtering of each masked data set along lines (t) generates a corresponding plurality of filtered data sets, where the data at each point along each line represents a summation of the Radon data at that point, as would have been developed by steps 1 through 5 of the Kudo et al 6-step process. Accordingly, the only step left to reconstruct the image is 3D backprojection, corresponding to Kudo et al's step 6. This 3D backprojection step can also be accomplished by computer 206, with the resultant image reconstruction appearing on display 220.

Although the single step of Feldkamp ramp filtering is much faster than using the prior art steps 1–5, there is a tradeoff, or price to pay, i.e., the developed Radon data is somewhat less accurate than needed to provide an exact image reconstruction. This is due the fact that when calculating the line integral derivative data in the Kudo et al 6-step process, there is no masking of the projection data. Likewise, in the modification of the Kudo et al process as described in K. Tam's forenoted patent application U.S. Ser. No. 09/052,281, there is no masking of the projection data, only of the extent of the line segments L for which line integral derivatives are calculated. That is, for example, as described in U.S. Ser. No. 09/052,281, line integrals for the adjacent line segments $L_1$ and $L_2$ are not masked, and in fact, the pixel values in detector rows above the detector rows that define the end points of the line segments L are used to exactly determine these line integrals (in a manner similar to that shown in FIGS. 5 and 6 in K. Tam's U.S. Pat. No. 5,748,697). Masking only takes place on the line segments L after the line integrals for line segments $L_1$ and $L_2$ have been subtracted to calculate the line integral derivatives for the line segments L. However, as a necessary consequence of ramp filtering of the masked projection data in accordance with image reconstruction processing of the present invention, it is implied that the extent of the line segments $L_1$ and $L_2$ are also limited by their intersection with the mask. A consequence of this implication is a somewhat less than exact reconstruction, but as a tradeoff there is an improved speed in the image reconstruction.

The present invention describes a technique for improving the exactness of the image reconstruction without significantly increasing the required amount of image reconstruction signal processing.

Figure 5:
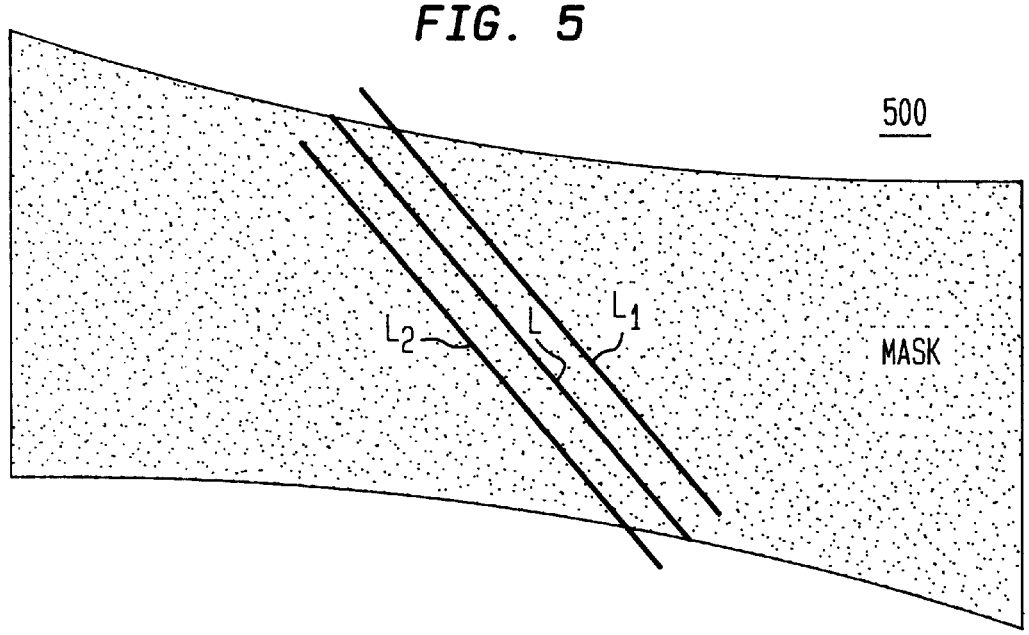

More specifically, by comparing FIG. 4 to FIG. 5, it can be seen that the difference between the corresponding line integrals in the two Figures appears only at the upper and lower mask boundaries, the line integrals on the rest of the line segments are identical. Thus the efficient ramp filtering method disclosed in K. Tam's forenoted U.S. patent application Ser. No. 09/106,537 can be used to compute a first estimate, or approximation, of the Radon derivative, implicitly using the integrals on line segments inside the mask, as shown in FIG. 4. Next, correction data is developed using, for example, the method disclosed in K. Tam's forenoted U.S. patent application Ser. No. 09/123,574 to compute the difference between line integrals at the mask boundaries. The correction data is then combined with the first estimate, thereby producing a more exact image reconstruction.

The determination of the correction data in accordance with the technique of the forenoted U.S. patent application Ser. No. 09/123,574 will now be described. The effect of the hard masking of FIG. 4 on the calculation of the line integral derivatives for lines L, corresponds to:

$$\left[\frac{d}{dr}\int L\right]HM = \frac{d}{dr}\int L = \int L'_2 - \int L'_1. \quad \text{(eq. 1)}$$

The effect of the soft masking of FIG. 5 on the calculation of the line integral derivatives for lines L, corresponds to:

$$\left[\frac{d}{dr}\int L\right]SM = \frac{d}{dr}\int L = \int L_2 - \int L_1. \quad \text{(eq. 2)}$$

Figure 10:
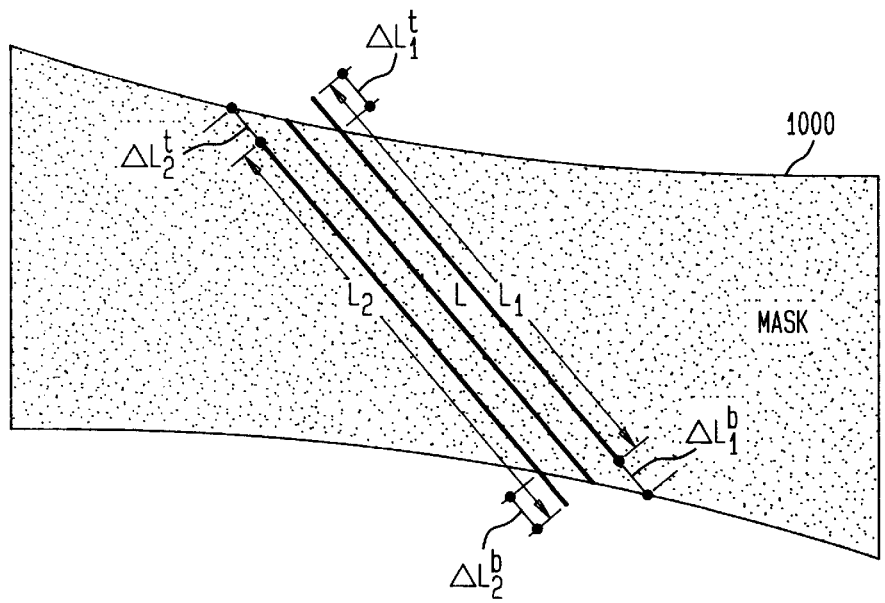
FIG. 10 is useful for illustrating the arithmetic difference between hard and soft masking, and for understanding how to develop more accurate Radon derivative data.

Referring jointly to FIGS. 4 and 10 (where FIG. 10 corresponds to FIG. 5, but with additional line segments ΔL shown on mask 1000 that are useful for indicating the difference in the length of the line segments that result during hard as compared with soft masking), equation 1 can be rewritten as:

$$\left[\frac{d}{dr}\int L\right]HM = \int L'_2 - \int L'_1 = \quad \text{(eq. 3)}$$

$$\left[\int L_2 + \int \Delta L'_2 - \int \Delta L^b_2\right] - \left[\int L_1 + \int \Delta L^b_1 - \int \Delta L'_1\right].$$

By appropriate collection of terms, equation 3 can be rewritten as:

$$\left[\frac{d}{dr}\int L\right]HM = \quad \text{(eq. 4)}$$

$$\left[\int L_2 - \int L_1\right] + \int \Delta L'_2 - \int \Delta L^b_2 - \int \Delta L^b_1 + \int \Delta L'_1$$

Substitution of equation 2 in equation 4 yields, $$\left[\frac{d}{dr}\int L\right]HM = \quad \text{(eq. 5)}$$

$$\left[\frac{d}{dr}\int L\right]SM + \left[\int \Delta L'_2 - \int \Delta L^b_2 - \int \Delta L^b_1 + \int \Delta L'_1\right].$$

By re-arranging terms, it is apparent that the exact Radon derivative data which results from soft masking may be realized by negatively combining the result of hard masking with correction data (CR), as shown below:

$$\left[\frac{d}{dr}\int L\right]SM = \quad \text{(eq. 6)}$$

$$\left[\frac{d}{dr}\int L\right]HM - \left[\int \Delta L'_2 - \int \Delta L^b_2 - \int \Delta L^b_1 + \int \Delta L'_1\right]CR$$

It is also noted that the correction data corresponds to the arithmetic difference between soft and hard masking.

Since the correction data only needs to be computed at the two mask boundary curves instead of over the entire detector, a ratio reduction in computation of the correction data of approximately 2/Nz, where Nz is the number of detector rows, is achieved.

Additionally, because the correction data are only computed for cone beam projection data acquired by detector pixels that intersect the mask boundaries, it becomes practical to use a pixel spread function table to speed up the computation. To generate the pixel spread function table, for each detector pixel (i,j) intersected by the mask boundary, one assign's a value of unity to the pixel and zero everywhere else. Next, one carries out the operations as indicated in FIG. 5. The resulting values are then backprojected (spread-out) over a "virtual detector" 2D space that has a height that is large enough to cover the entire field of view of the object. The 2D information resulting from this process constitutes a normalized pixel spread function table for the boundary pixel (i,j). Note that the pixel spread function table covers the virtual detector rather than the actual (short) detector, because backprojection from each line segment should be extended to the entire plane Q(r,θ), as demanded by the mathematics of Radon inversion. In operation, the additive combination of each boundary pixel (i,j) to the 2D correction data is simply and quickly determined by merely multiplying the intensity value of the cone beam projection data at each boundary pixel (i,j) with the values of its pixel spread function table, and additively combining the results obtained for each boundary pixel (i,j) in a common 2D virtual detector space. Note, as is conventional, the intensity value used for the data at each boundary pixel (i,j) is preferably a fraction of the actual intensity value of the pixel, which fraction corresponds to the percentage of that pixel's area that is inside the mask.

Since there are approximately Nx pixels on the mask boundary, and the pixel spread function table for each pixel has Nx by Ny entries (where Nx by Ny are the dimensions of the virtual detector), the size of the entire pixel spread function table is Nx by Nx by Ny. Thus, the table is quite large. Several techniques are described in the forenoted U.S. patent application Ser. No. 09/123,574 for reducing the size of the table. For example, the same table can be used for the mask boundary pixel data acquired from all of the source positions in the interior of the spiral path (because these mask boundaries all have the same shape). Furthermore, because the bottom mask boundary is the reflection of the top mask boundary about the origin, i.e. (x,y) →(−x,−y), a pixel spread function table only needs to be computed for one of these boundaries, thereby achieving a further reduction factor of 2 in the size of the table.

Furthermore, examination of the masks for source positions near the circle scans for ROI imaging, as illustrated in FIGS. 7 and 8, indicates how further reductions in the size of the pixel spread function table are possible. For those pixels on portions 802 and 804 of mask 800, the same pixel spread function table can be used as was used for the upper and lower boundaries of mask 500. It is obvious that all the pixels on the horizontal line 702 in FIG. 7 have the same pixel spread function table, and thus only an additional Nx by Ny entries are needed for line 702. For those pixels that are on the lower boundary 704 in FIG. 7 (which is the projection of the immediately adjacent spiral scan path segment from the source positions on the circle scan path), and the upper boundary 806 in FIG. 8 (which is the projection of the circle scan path from the source positions on the immediately adjacent spiral scan path segment), the correction data can be computed directly using the method illustrated in FIG. 5. In a typical spiral scan most of the views involve the standard spiral mask illustrated in FIG. 4, and the number of views involving the boundaries 704 and 806 is small in comparison. Thus the time spent on computing the corrections related to boundaries 704 and 806 is also small.

Figure 1A:
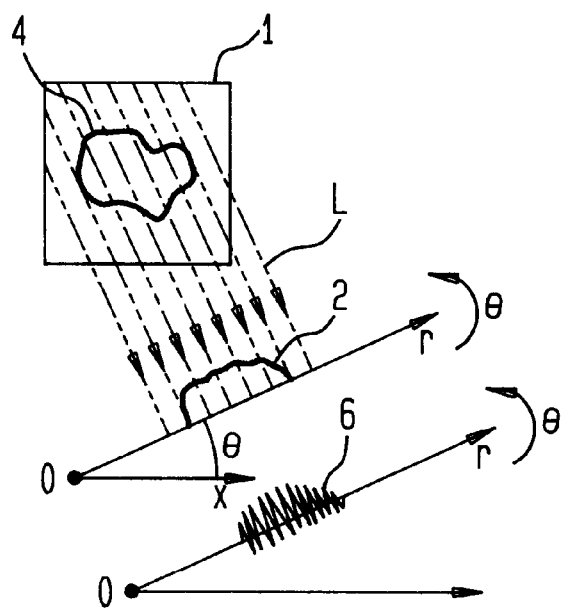
FIGS. 1A and 1B illustrate the Kudo et al. prior art 3D backprojection approach for cone beam image reconstruction, previously described.
Figure 1B:
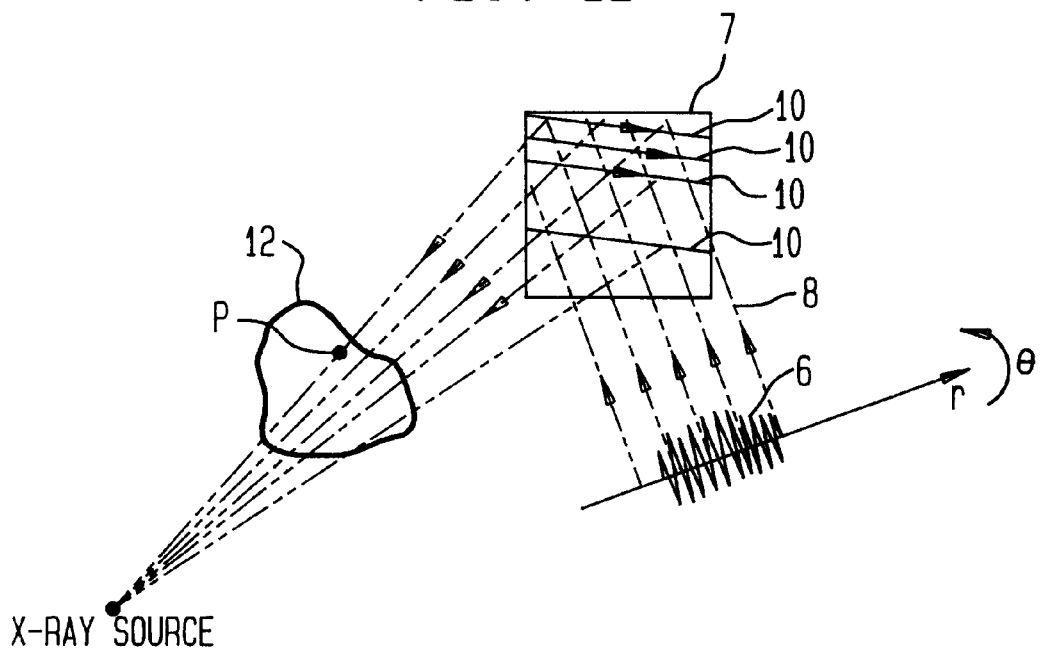

The combination of the 2D correction data with the 2D first estimate data can be made before the 3D weighted backprojection step (i.e., by combining both sets of the 2D data in a common 2D space, such as space 7 shown in FIG. 1B for the first estimate data and that portion of space 7 that overlaps with the virtual detector space for the correction data), or the first estimate data and the correction data can be individually subjected to 3D weighted backprojection from their own 2D spaces into a common 3D space, such as space 12 shown in FIG. 1B. Note that in either case, the correction data must be backprojected into a 2D space corresponding to the size of the virtual detector, i.e., one that would have been large enough to acquire a complete field of view of the ROI in the object at a single source position.

In accordance with the present invention, a technique is provided to achieve a significant reduction in the amount of 2D correction data needed for image reconstruction, without significantly decreasing the exactness of the reconstructed image. Accordingly, the present invention achieves a significant reduction in the amount of signal processing required for image reconstruction, with a concomitant increase in the speed of the image reconstruction.

More specifically, recall that in connection with equation (6) above, correction data is calculated for each of a great plurality of line segments L(r, θ) and then the correction data calculated for each of the line segments is backprojected at its angle θ into a 2D space having a size corresponding to the virtual detector. The present inventors have realized that for each angle θ, the magnitude of the correction data, and hence the magnitude of the backprojection result p(r, θ), is dependant upon the angle θ that L makes with the mask boundary. As is apparent from examination of FIG. 10, the smaller the angle θ that L(r, θ) makes with the mask boundary, the longer the line segment ΔL which extends past the mask boundary, and the greater the value of the correction data calculated using that ΔL. Conversely, the greater the angle θ that L(r, θ) makes with the mask boundary (i.e., as it approaches 90°), the shorter the line segment ΔL which extends past the mask boundary, and the smaller the value of the correction data calculated using that ΔL.

Accordingly, the lesser or greater the angle θ that L(r, θ) makes with the mask boundary, the greater or lesser the value of the 2D correction data. This is graphically illustrated by FIG. 11, where 1100 indicates an illustrative mask boundary, 1102 indicates an illustrative "value of correction data" ΔL(r, θ) waveform where the angles θ that L(r, θ) makes with the mask boundary are relatively small (as evident from the indicated angle that backprojection direction arrows 1104 make with mask 1100), and 1106 indicates an illustrative "value of correction data" ΔL(r, θ) waveform, where the angles θ that L(r, θ) makes with the mask boundary are relatively large, i.e., near 90° (as evident from the indicated angle that backprojection direction arrows 1108 make with mask 1100).

It is apparent that the magnitude of ΔL(r, θ) is low in those directions (θ) at, or close to, a right angle to the mask boundary, and low in those directions parallel to the mask boundary. In a typical cone beam CT imaging system, the mask boundaries are usually at a small angle to the x axis for a typical spiral pitch. Consequently the magnitude of ΔL(r, θ) is high for θ at small angles to the x axis, and consequently the mask boundaries (as shown by ΔL waveform 1102), and low for (θ) at, or close to, a right angle to the mask boundary (as shown by ΔL waveform 1106).

Accordingly, the dominant contributions to the 2D correction data come from ΔL's at a small angle θ to the x axis(as shown by ΔL waveform 1102). However, as it is apparent by examination of FIG. 11, the value of the backprojection result p(r, θ) near the top and bottom edges of the 2D correction data space (x,y) are formed from backprojecting at small angles θ to they axis. Since the values for ΔL waveform 1106 are relatively low in magnitude at those angles, so are the backprojection result p(r, θ), i.e., the 2D correction data. Thus the values near the top and bottom edges of the 2D correction data space (x,y) are very low in magnitude. Consequently the magnitude of the 2D correction data drops off fairly sharply in they direction away from the masked region. The sharpness of the drop-off in contribution to the 2D correction data is illustrated in FIG. 12, which is a plot of the function tanθ, representing an approximation of the changes in the ΔL(r, θ) as a function of the angle θ, when the mask boundary is assumed to be a horizontal line.

As a consequence of the above, there are two implications:

1. The 2D correction data can be developed to a very good approximation using only those p(r, θ) that are at small angle intersections to the x axis, and
2. When performing the 3D backprojection step, instead of developing and backprojecting the 2D correction data from a 2D space corresponding to the size of the virtual detector, as a consequence of implication (1) above, the 2D space can be trimmed off outside, or just a little beyond, the size of the actual detector containing the masked region without any substantial loss of 2D correction data, and thereby without any significant effect on the exactness of the image reconstruction.

Thus, in accordance with the principles of the present invention, the signal processing required for developing and then 3D backprojecting the 2D correction data can be reduced from developing and then processing data that covers the entire virtual detector to only the data that covers the actual detector, plus a strip of data at the top and bottom edges of the actual detector. The size of the top and bottom strips are adjustable depending on the desired degree of accuracy in the final image reconstruction. With the present invention, it is believed that, for example, by reducing the vertical height of a 1000 pixel by 1000 pixel virtual detector from 1000 pixels to 600 pixels, a 40% reduction in signal processing, and hence image reconstruction speed, can be achieved, with only a 5% decrease in the degree of image reconstruction accuracy.

In a preferred implementation of the invention, during operation of the imaging apparatus the user will input to computer 206 (using a keyboard, not shown) the desired degree of accuracy of the reconstructed image (or equivalently, a desired reconstruction speed), and based thereon, during image reconstruction processing the computer will determine the corresponding height of the virtual detector to be used for the 2D backprojection to develop the 2D correction data. Accordingly, when the user selects the highest degree of accuracy computer 206 sets a height for the virtual detector sufficient to cover the entire ROI, when the user selects the lowest degree of accuracy computer 206 sets a height for the virtual detector corresponding to the height of the actual detector, and for intermediate degrees of accuracy, correspondingly intermediate heights are selected for the virtual detector.

Figure 11:
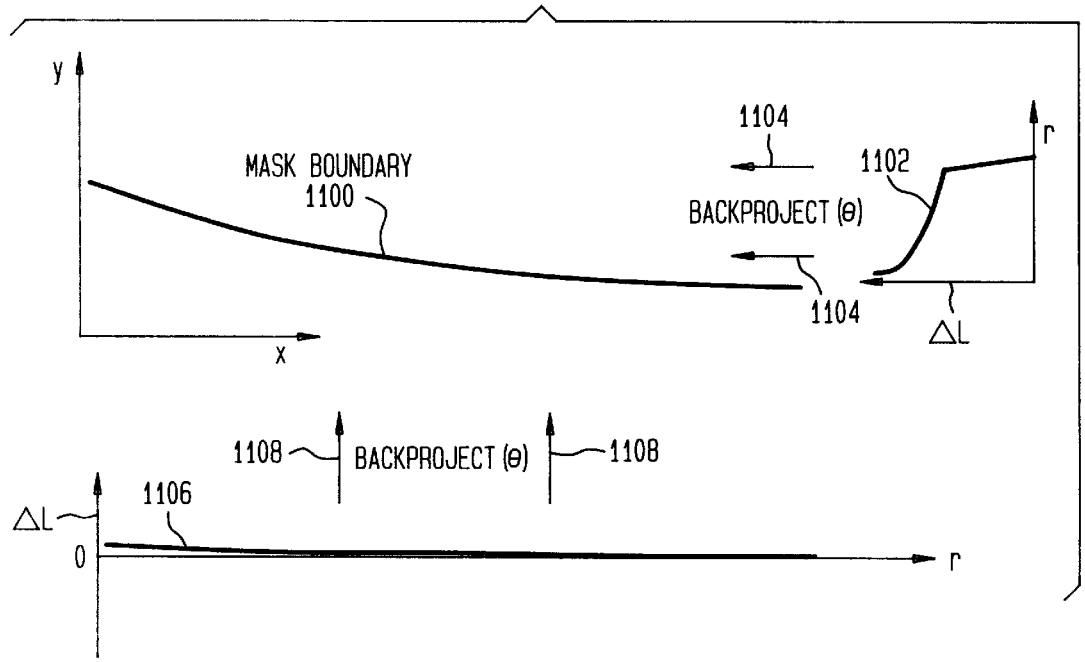
FIG. 11 illustrates the relative amount of correction data that is developed as a function of the angle the backprojection direction makes with the mask boundaries.
Figure 12:
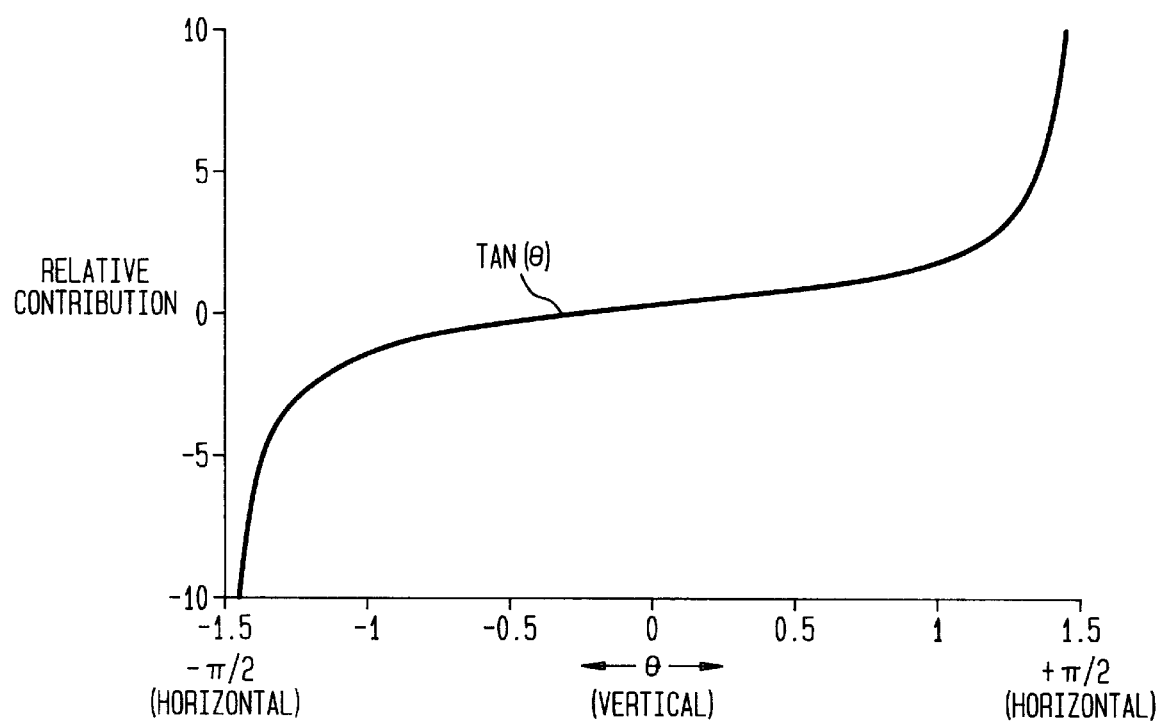
FIG. 12 illustrates the relative value of the contribution to the Radon derivative data from the correction data, as a function of the angle the backprojection direction makes with the mask boundaries.

Commensurate with implication (1) above, and upon further consideration of FIG. 11, it can be seen that instead of adjusting the height of the virtual detector as a tradeoff between laborious signal processing and a user determined desired degree of reconstruction accuracy or speed, the same result can also be achieved by limiting the calculation of the correction data to a predetermined limited range of angles (θ) associated with both the calculation of the $\Delta L(r,\theta)$ data, as well as its 2D backprojection into the virtual detector space. This will result in a significant savings in signal processing to calculate the $\Delta L(r,\theta)$ correction data, as well as a significant savings in the signal processing required for 2D and then 3D backprojection of this correction data. More specifically, by limiting the range of angles for calculating the $\Delta L(r,\theta)$ data to a user determined range, e.g., 0–20 degrees with the x axis (the approximate range of angles shown in waveform 1102 in FIG. 11), and then limiting the 2D backprojection angle of this limited amount of data to the same user determined angular range, one would achieve a significant savings in signal processing (and a corresponding increase in the speed of the image reconstruction), while still obtaining a substantial amount of 2D correction data and therefore suffer a relatively insignificant loss in reconstruction accuracy. It is noted that as a consequence of using a limited range of angles, the 2D correction data is concentrated in the 2D detector space just outside the mask boundaries. Accordingly, during the 3D backprojection, computer 206 will preferably limit, i.e., reduce, the size of the virtual detector towards the size of the actual detector by an amount commensurate with the expected degree of concentration of the 2D correction data. Consequently, during the image reconstruction processing, computer 206 will preferably use a combination of both of the above techniques to simplify and speed up the signal processing, while still obtaining a substantially high desired degree of image reconstruction accuracy.

Thus, there has been shown and described a novel method and apparatus for controlling the exactness of image reconstruction in a cone beam CT imaging apparatus using a simplified 3D backprojection image reconstruction. Many changes, modifications, variations and other uses and applications of the subject invention will, however, become apparent to those skilled in the art after considering this specification and its accompanying drawings, which disclose preferred embodiments thereof. For example, instead of the user specifying a limited range of angles, the user may, like in the first noted preferred embodiment, specify a desired degree of accuracy, and then computer 206 will adjust the image reconstruction processing by using a predetermined limited range of angles, and/or virtual detector sizes, that is matched to achieve the user specified degree of image reconstruction accuracy. Furthermore, the principles of the invention, such as the adaptive limitation of the range of angles θ related to the generation and then 2D backprojection of the correction data, can be incorporated in whole or part into the generation of the "pixel spread function table", so that, for example pixel spread function tables representing varying degrees of tradeoff between image reconstruction speed and accuracy can be precalculated and stored for use during operation of the imaging system. All such changes, modifications, variations and other uses and applications which do not depart from the teachings herein are deemed to be covered by this patent, which is limited only by the claims which follow as interpreted in light of the foregoing description.

What is claimed is:

1. A method for three dimensional (3D) computerized tomographic (CT) imaging of a region-of-interest (ROI) in an object, comprising:

acquiring a plurality of sets of 2D cone beam projection data by irradiating the object with energy from a cone beam source that is directed toward a 2D detector at a corresponding plurality of scan path source positions located about the object;

applying a mask to each set of the 2D cone beam projection data to form a corresponding plurality of masked 2D data sets;

processing the 2D cone beam projection data inside the mask boundaries of each masked 2D data set to develop a corresponding plurality of processed 2D data sets, each processed 2D data set corresponding to a calculation of a first estimate of Radon derivative data determined for a given set of the 2D cone beam projection data;

adaptively developing a predetermined limited amount of 2D correction data for each of the first estimates of Radon derivative data; and combining each processed 2D data set and the 2D correction data adaptively developed therefore, in a weighted 3D backprojection manner into a common 3D space, thereby reconstructing in said 3D space a 3D image of the ROI in the object.

2. The method of claim 1, wherein the processing of the 2D cone beam projection data inside the mask boundaries comprises Feldkamp ramp filtering of said data along a plurality of parallel lines formed therein.

3. The method of claim 1, wherein the adaptiveness of the predetermined limited amount of 2D correction data that is developed is based on one of a desired degree of image reconstruction accuracy or a desired image reconstruction speed.

4. The method of claim 1, wherein the developing of said 2D correction data includes adaptively processing portions of the given set of 2D cone beam projection data that are adjacent boundaries of the mask in a corresponding one of the masked 2D data sets.

5. The method of claim 1, wherein the processing step corresponds to determining line integral derivatives for the 2D cone beam projection data in the masked 2D data sets that lies along a plurality of line segments L(r,θ) having their end points bound by the mask in each of the masked 2D data sets.

6. The method of claim 5, wherein the developing of said 2D correction data includes calculating $\Delta L(r,\theta)$ derivative data corresponding to the difference between line integrals calculated for pairs of line segments ΔL(r,θ) that are adjacent top and bottom boundaries of each mask, which pairs of line segments ΔL(r,θ) result from equal and opposite orthogonal translation of the line segments L(r,θ) and extend outside and inside, respectively, of the top and bottom boundaries of the mask.

7. The method of claim 6, wherein the developing of said 2D correction data includes backprojecting the ΔL(r,θ) derivative data into a 2D space along a corresponding backprojection direction (θ).

8. The method of claim 6, wherein the developing of said 2D correction data includes processing an adaptively limited range of angles (θ) for the calculated ΔL(r,θ) derivative data, the adaptiveness of said range being based on one of a desired degree of image reconstruction accuracy or a desired image reconstruction speed.

9. The method of claim 7, wherein the backprojecting of the ΔL(r,θ) derivative data is along an adaptively limited range of backprojection directions (θ), the adaptiveness of said limited range being based on one of a desired degree of image reconstruction accuracy or a desired image reconstruction speed.

10. The method of claim 6, wherein the developing of said 2D correction data includes backprojecting the ΔL(r,θ) derivative data into a 2D space having a size that is adaptively determined.

11. The method of claim 10, wherein the adaptiveness of said size determination during the backprojecting of the ΔL(r,θ) derivative data is based on one of a desired degree of image reconstruction accuracy or a desired image reconstruction speed.

12. The method of claim 4, wherein the developing of said 2D correction data includes multiplying portions of the 2D cone beam projection data that intersect top and bottom boundaries of the mask by a pixel spread function table that has been adaptively predetermined for said portions of the 2D cone beam projection data.

13. The method of claim 12, wherein the adaptiveness of the pixel spread function table is based on one of a desired degree of image reconstruction accuracy or a desired image reconstruction speed.

14. The method of claim 12, wherein said pixel spread function table is adaptively predetermined by determining line integral derivatives for only a limited angular range (θ) for line segments ΔL(r,θ).

15. The method of claim 14, wherein said pixel spread function table is adaptively predetermined by 2D backprojecting said determined line integral derivatives along only a limited angular range (θ) of backprojection directions.

16. The method of claim 14, wherein said pixel spread function table is adaptively predetermined by 2D backprojecting said determined line integral derivatives into a 2D space having an adaptively determined size.

17. The method of claim 16, wherein the adaptiveness of the size of the 2D space is based on one of a desired degree of image reconstruction accuracy or a desired image reconstruction speed.

18. Apparatus for three dimensional (3D) computerized tomographic (CT) imaging of a region-of-interest (ROI) in an object, comprising:
- a cone beam source for applying radiation energy to at least the ROI of the object;
- a 2D area detector for detecting radiation energy;
- means for defining a source scanning trajectory as a scan path traversed by the source;
- a manipulator for causing the cone beam source, fixed relative to an area detector with both source and detector movably positioned relative to the object, to scan about the ROI in the object at a plurality of source positions in a direction along the scan path to cause said area detector to acquire a set of 2D cone beam projection data at each of said source positions;
- a masking means for applying a mask to each set of the 2D projection data to form masked data sets;
- estimating means for processing the 2D cone beam projection data inside the mask boundaries of each masked 2D data set along a plurality of parallel lines formed therein, to generate a corresponding plurality of estimated 2D data sets, each estimated 2D data set corresponding to a calculation of a first estimate of Radon derivative data determined for a given set of the 2D cone beam projection data;
- an adaptive processor means for adaptively developing a predetermined limited amount of 2D correction data for each of the first estimates of Radon derivative data; and
- 3D backprojection means for combining each estimated 2D data set and the 2D correction data adaptively calculated therefore, in a weighted 3D backprojection manner into a common 3D space, thereby reconstructing in said 3D space a 3D image of the ROI in the object.

19. The apparatus of claim 18, wherein the estimating means comprises a ramp filter processor for ramp filtering the 2D cone beam projection data inside the mask boundaries of each masked 2D data along a plurality of parallel lines formed therein.

20. The apparatus of claim 18, wherein the adaptive processor develops the predetermined limited amount of 2D correction data based on one of a desired degree of image reconstruction accuracy or a desired image reconstruction speed.

21. The apparatus of claim 18, wherein adaptive processor develops the predetermined limited amount of 2D correction data by processing portions of the given set of 2D cone beam projection data that are adjacent boundaries of the mask in a corresponding one of the masked 2D data sets.

22. The apparatus of claim 21, wherein the estimating means determines line integral derivatives for the 2D cone beam projection data in each of the masked 2D data sets that lies along a plurality of line segments L(r,θ), each line segment having its end points bound by the mask in each of the masked 2D data sets.

23. The apparatus of claim 22, wherein the adaptive processor calculates ΔL(r,θ) derivative data as said correction data, said derivative data corresponding to the difference between line integrals calculated for pairs of line segments ΔL(r,θ) that are adjacent top and bottom boundaries of each mask, which pairs of line segments ΔL(r,θ) result from equal and opposite orthogonal translation of the line segments L(r,θ) and extend outside and inside, respectively, of the top and bottom boundaries of the mask.

24. The apparatus of claim 23, wherein the adaptive processor backprojects the ΔL(r,θ) derivative data into a 2D space along a corresponding backprojection direction (θ).

25. The apparatus of claim 23, wherein the adaptive processor processes an adaptively limited range of angles (θ) for the calculated ΔL(r,θ) derivative data, the adaptiveness of said range being based on a one of a desired degree of image reconstruction accuracy or a desired image reconstruction speed.

26. The apparatus of claim 24, wherein the adaptive processor backprojects the ΔL(r,θ) derivative data along an adaptively limited range of backprojection directions (θ), the adaptiveness of said limited range being based on one of a desired degree of image reconstruction accuracy or a desired image reconstruction speed.

27. The apparatus of claim 24, wherein the adaptive processor backprojects the ΔL(r,θ) derivative data into an adaptively determined size for said 2D space.

28. The apparatus of claim 27, wherein the adaptive processor determines the size of said space based on one of a desired degree of image reconstruction accuracy or a desired image reconstruction speed.

29. The apparatus of claim 21, wherein the adaptive processor includes a memory for storing values for a pixel spread function table that has been adaptively predetermined for portions of the 2D cone beam projection data that intersect top and bottom boundaries of the mask, the adaptive processor multiplying portions of the 2D cone beam projection by the values of said pixel spread function table.

30. The apparatus of claim 29, wherein the adaptiveness of the pixel spread function table is based on one of a desired degree of image reconstruction accuracy or a desired image reconstruction speed.

31. The apparatus of claim 29, wherein the adaptiveness of the pixel spread function table is predetermined by determining line integral derivatives for only a limited angular range (θ) for line segments ΔL(r,θ).

32. The apparatus of claim 31, wherein said pixel spread function table is adaptively predetermined by 2D backprojecting said determined line integral derivatives along only a limited angular range (θ) of backprojection directions.

33. The apparatus of claim 31, wherein said pixel spread function table is adaptively predetermined by 2D backprojecting said determined line integral derivatives into a 2D space having an adaptively determined size.

34. The apparatus of claim 31, wherein said pixel spread function table adaptively predetermines the size of the 2D space based on one of a desired degree of image reconstruction accuracy or a desired image reconstruction speed.

* * * * *